United States Patent [19]

Dibie et al.

[11] Patent Number: 5,413,586
[45] Date of Patent: May 9, 1995

[54] ANTI-PULMONARY EMBOLISM FILTER AND CORRESPONDING PRESENTATION AND FITTING KIT

[75] Inventors: Alain Dibie, Paris; Dominique Musset, Clamart; Philippe Prou; Gilles Catteau, both of Auneau Cedex, all of France

[73] Assignee: Ethnor, Neuilly-sur-Seine Cedex, France

[21] Appl. No.: 117,131

[22] PCT Filed: Mar. 12, 1992

[86] PCT No.: PCT/FR92/00224
§ 371 Date: Sep. 14, 1993
§ 102(e) Date: Sep. 14, 1993

[87] PCT Pub. No.: WO92/16163
PCT Pub. Date: Oct. 1, 1992

[30] Foreign Application Priority Data

Mar. 14, 1991 [FR] France .................. 91 03103
Nov. 19, 1991 [FR] France .................. 91 14231

[51] Int. Cl.⁶ .......................................... A61M 29/00
[52] U.S. Cl. ................................ 606/200; 128/899
[58] Field of Search ............ 606/191, 195, 198, 200; 623/1, 12; 604/104–106; 128/898, 899

[56] References Cited

U.S. PATENT DOCUMENTS 4,994,069 2/1991 Ritchart et al. .

FOREIGN PATENT DOCUMENTS 0121447 10/1984 European Pat. Off. .
0323333 7/1989 European Pat. Off. .
2616666 12/1988 France .
2645731 10/1990 France .
3203410 11/1982 Germany .

OTHER PUBLICATIONS

Cragg, Martin, et al. "Nitinol Spiral Vena Caval Filter". Seminars In Interventional Radiology. vol. 3, No. 3, Sep. 1986.

*Primary Examiner*—Stephen C. Pellegrino
*Assistant Examiner*—William W. Lewis
*Attorney, Agent, or Firm*—Jacobson, Price, Holman & Stern

[57] ABSTRACT

The invention describes a pulmonary embolism prevention filter of the type made from an elastic wire with remanent spring effect, characterized int hat it comprises at least two wires (100, 200), each spirally shaped. The said two wires (100, 200) have at least substantially the same length and are connected in the vicinity of their ends.

63 Claims, 10 Drawing Sheets

FIG_1

FIG_2

FIG_7

FIG_8

ANTI-PULMONARY EMBOLISM FILTER AND CORRESPONDING PRESENTATION AND FITTING KIT

The present invention relates to the field of anti-pulmonary embolism filters.

More precisely, the present invention relates to improvements to the anti-pulmonary embolism filter described in French Patent Applications No. 89 13160 of 9, Oct. 1989 and No. 89 16538 of 14, Dec. 1989 and PCT Patent Application No. PCT/FR90/00721 filed on 9, Oct. 1990.

Various anti-pulmonary embolism filters have already been proposed. Regarding this point, reference may be made for example to documents FR-A-2,616,666, EP-A-121,447, EP-A-323,333 and DE-A-3,203,410.

The anti-pulmonary embolism filters described in the aforementioned documents are not however completely satisfactory.

Document EP-A-323,333 in particular describes a filter made of resilient metal wire with spring effect.

Its particular geometrical shape defines two loops in the shape of ellipses with perpendicular, equal and coplanar axes, giving four points of permanent contact with the wall of the vena cava in which it is implanted.

This latter type of filter has actually been the subject of production and experimentation on animals, and then on man. However, such difficulties of medical nature appeared, both in the procedure for fitting the filter and in its mode of operation once in place, that general use of this filter cannot be recommended medically.

More precisely, a first difficulty resides in that the filter, which initially has the aforementioned shape of double ellipses with perpendicular axes, after its temporary straightening inside the fitting catheter, sometimes risks, when released from the catheter, inside the inferior vena cava, not resuming its initial shape. This drawback results from fairly long quasi-straight parts which connect the quasi-circular parts of the elongate quasi-ellipses. Thus, there are unacceptable risks of the filter returning to the shape of an elongate S or 8, and no longer of crossed ellipses. Bearing against the walls of the vena cava at four balanced points is not obtained and, because of this, the vein is not sufficiently flattened, so that the filter can migrate by moving along the vein after it is fitted.

Furthermore, the planes of these ellipses are quasi-coplanar, and the filter effect is guaranteed only if the four points of bearing of the filter against the wall of the vena cava are in the correct position, which is not yet guaranteed as explained above, on the one hand, and very greatly flatten the vena cava in order greatly to reduce the cross-section of the vein and thus to obtain the filter effect, on the other hand.

Finally, one end of the filter is fitted with a sharp tip which is inclined with respect to the plane of the ellipses and is used as an anchoring point in the vena cava. This sharp tip has two drawbacks: it makes it difficult to introduce it into the catheter, on the one hand, and risks traumatizing or even perforating the wall of the vein, on the other hand.

The filter described in French Patent Applications No. 89 13160 of 9, Oct. 1989 and No. 89 16538 of 14, Dec. 1989, as well as in the corresponding PCT Patent Application No. PCT/FR90/00721 of 9, Oct. 1990, made it possible to improve this situation. This filter comprises a resilient wire with remanent spring effect shaped into a spiral with three non-touching turns, the middle turn of which has a diameter greater than those of the other two turns, the diameter of the middle turn being preferably chosen close to the value of half the circumference of the vena cava in the zone where the filter is to be implanted, in order optimally to ensure the function of holding the filter in place by flattening the vena cava.

The object of the present invention is further to improve the filter of the aforementioned type by improving the filtering effect obtained, whilst allowing both easy fitting and withdrawal of the filter.

This object is achieved according to the present invention by virtue of the structure defined in the attached claim 1.

Other features, objects and advantages of the present invention will emerge on reading the detailed description which follows, and in the light of the attached drawings which are given by way of non-limiting examples, and in which.

Figure 1:
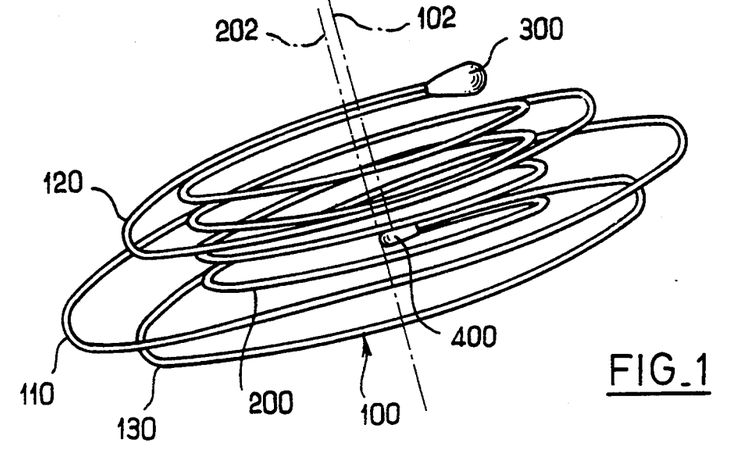
FIG. 1 represents a diagrammatic perspective view of an anti-pulmonary embolism filter in accordance with a preferred embodiment of the present invention.
Figure 2:
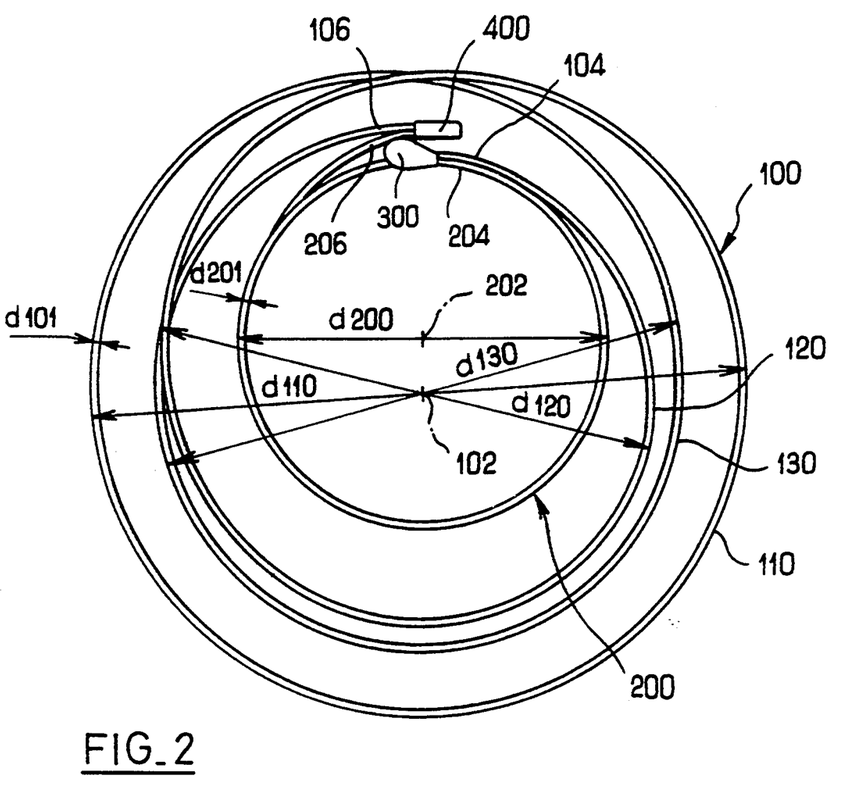
FIG. 2 represents a top view of the same filter in accordance with the preferred embodiment of the present invention.
Figure 3:
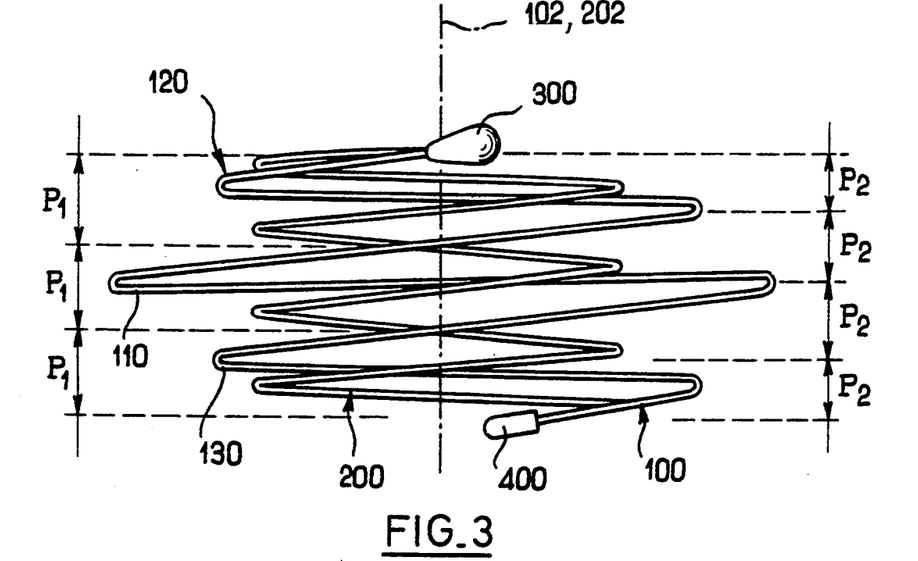
FIG. 3 represents a side view of the same filter in accordance with the present invention, FIGS. 4, 5 and 6 diagrammatically represent, in the semi-straight stretched state, the wires forming three variant embodiments of the filter in accordance with the present invention.

FIRST EMBODIMENT OF THE FILTER REPRESENTED IN FIGS. 1 TO 3

A description will first of all be given of the embodiment of the anti-pulmonary embolism filter represented in FIGS. 1 to 3.

The filter represented in FIGS. 1 to 3 is formed by two separate wires 100, 200, each shaped into a non-planar spiral.

Even more precisely, the wire 100 forms a spiral with three turns: a middle turn 110 and two lateral turns 120, 130. The three turns 110, 120, 130 are non-touching. The middle turn 110 has a diameter d110 greater than the mean diameters d120, d130 of the two lateral turns 120, 130. The two lateral turns 120, 130 preferably have mean diameters d120, d130 which are identical or substantially identical.

As is clearly seen on examining FIG. 2, the three spirals 110, 120, 130 are approximately coaxial and centered on an axis 102 orthogonal to the plane of FIG. 2. Preferably, the diameter d110 of the middle turn 110 is greater than 1.25 times the diameter d120, d130 of the lateral turns 120, 130. Highly advantageously, the diameter d110 of the middle turn 110 is greater than 1.4 times the diameter d120, d130 of the lateral turns 120, 130.

The three turns 110, 120, 130 preferably have substantially identical pitches.

The pitch p1 of the spiral formed by the wire 100 is at least of the order of 3 mm, preferably at least of the order of 7 mm, highly preferably at least of the order of 9 mm at rest, before implantation. Thus, the total axial thickness of the spiral formed by the wire 100 is at least approximately 9 mm, preferably approximately 21 mm, highly preferably approximately 27 mm at rest, whatever the value of the diameter d110 of the larger middle turn 110.

The size of the filter must be adapted to the vena cava to be equipped. For this purpose, the diameter d110 of the largest middle turn 110 must be as close as possible to half the value of the circumference of the inferior vena cava. Thus, the middle turn 110 always has a diameter d110 greater than that of the vena cava, in order to obtain a flattening effect of the vena cava when fitting the filter.

In practice, it is possible to choose a filter size 1 in which the diameter d110 of the middle turn 110 is of the order of 27 mm for venae cavae of diameter 16 to 18 mm. It is possible to choose a filter size 2 in which the diameter d110 of the middle turn 110 is of the order of 31.5 mm for venae cavae diameters of 19 to 21 mm. It is possible to choose a filter size 3 in which the diameter d110 of the middle turn 110 is of the order of 36 mm for venae cavae diameters of 22 mm to 23 mm.

Finally, it is possible to choose a filter size 4 in which the diameter d110 of the middle turn 110 is of the order of 40 mm for venae cavae of larger diameters.

The ends of the filter, that is to say the ends of the wire 100, are radiopaque to X-rays, in order to be clearly visible under a luminance amplifier. This arrangement has the object of facilitating monitoring of the fitting of the filter. For this purpose, the ends of the wire 100 may be fitted with endpiece [sic] 300, 400 as will be described in more detail below.

The second wire 200 forms a second spiral. Preferably, the second spiral formed by the wire 200 comprises a plurality of turns of identical diameter d200. Furthermore, the length of the second wire 200 is at least substantially equal to the length of the first wire 100. The second spiral formed by the wire 200 preferably has a constant or substantially constant pitch p2. The number of turns of the second spiral formed by the wire 200 consequently depends on the diameter d200 of the turns of the second spiral. By way of non-limiting example, the second spiral formed by the wire 200 has four turns. According to an advantageous characteristic of the present invention, the mean diameter d200 of the turns of the second spiral formed by the wire 200 lies between two-thirds and half the diameter d110 of the larger turn 110 of the first spiral.

Thus, for example, the second spiral formed by the wire 200 typically has a mean diameter d200 lying between 14 and 24 mm, highly advantageously lying between 20 and 24 mm.

According to the embodiment represented in FIGS. 1 to 3, the two spirals formed respectively by the wires 100 and 200 are of the same sign of helical twisting, that is to say of the same handedness.

According to another advantageous characteristic of the present invention, the wire 200 forming the second spiral of constant diameter d200 is more flexible than the wire 100 forming the first spiral. For this purpose, the wire 200 preferably has a diameter smaller than that of the filter 100. The second spiral 200 is centered on an axis 202 orthogonal to the plane of FIG. 2. The axis 202 is off-centered with respect to the axis 102 of the first spiral, and parallel to it.

A first end 104 of the first spiral is fixed to a first end 204 of the second spiral 200, whilst the second end 106 of the first spiral is fixed to the second end 206 of the second spiral.

The two wires 100, 200 may be connected, by their respective ends, using any appropriate conventional means. The wires 100, 200 may thus be connected by adhesive bonding or soldering at their ends.

However, according to a preferred embodiment, the two wires 100, 200 are connected together, at their ends, by crimping in the endpieces 300, 400.

These endpieces 300, 400 can form the subject of numerous embodiments.

They are preferably generally rounded bodies so as to avoid injuring the vena cava.

In the rest of the text, the term "proximal end" will be used to denote the end of the filter formed by the ends 104 and 204 of the wires 100, 200. Moreover, the end formed by the ends 106 and 206 of the wires will be termed the "distal end" of the filter.

According to the embodiment represented in FIGS. 1 to 3, the endpiece 300 has an ovoid teardrop shape, rounded towards its free end part and conical at its end part crimped onto the ends 104 and 204 of the wires 100, 200. This shape makes it possible for it to be moved in both directions within the lumen of a fitting catheter without damaging the latter and without constraint. The ovoid teardrop shape of the endpiece 300 also makes it possible to avoid any injury to the inferior vena cava. Finally, the ovoid teardrop shape of the endpiece 300 makes it possible to reintroduce the filter without difficulty into a withdrawal catheter, if necessary, without abutting against the entry orifice of the catheter.

By way of non-limiting example, the dimensions of the endpiece 300 may be 1.3 mm for its larger diameter and 0.7 mm for its diameter for attachment onto the wires 100, 200, the length of the endpiece 300 being of the order of 3.5 mm.

The second endpiece 400 may be identical to the endpiece 300 previously described, that is to say may have an ovoid teardrop shape.

However, according to the particular embodiment represented in FIGS. 1 and 2, the second endpiece 400 has the shape of a small cylinder with rounded ends. By way of non-limiting example, the cylinder 400 has an external diameter of the order of 0.8 mm and a length of the order of 4 mm. It is crimped onto the distal ends 106, 206 of the wires 100 and 200.

If required, the endpiece 300 first mentioned may be identical to the endpiece 400: that is to say that the endpiece 300 may be formed by a small cylinder with rounded ends.

The endpieces 300, 400 may be provided with a single hole accommodating both the proximal ends 104 and 204 of the wires 100, 200 or the distal ends 106, 206 of the latter. As a variant, the endpieces 300, 400 may each be provided with two holes, respectively accommodating the proximal ends 104, 204 or the distal ends 106, 206 of the wires.

According to the embodiment represented in FIGS. 1 to 3, the wires 100 and 200 have a curvature which is substantially regular and continuous over their entire length. The result of this is that, once the filter is fitted, the endpieces 300 and 400 rest against the internal surface of the inferior vena cava.

In order to facilitate withdrawal of the filter by grasping one of its endpieces 300, 400, preferably at least one of the proximal ends of the filter has a curvature discontinuity, and for this purpose converges both in the direction of the axis 102 of the first spiral and in the direction of the middle turn 110 of larger diameter. By virtue of this, after implantation of the filter, at least a corresponding one of the endpieces 300, 400 remains at a distance from the internal surface of the inferior vena cava, which facilitates gripping of this endpiece with a view to withdrawing the filter using means as described in French Patent Applications No. 89 13160 of 9, Oct. 1989, No. 89 16538 of 14, Dec. 1989 or alternatively by the means represented in FIGS. 17 to 28, which will be described in more detail in the rest of the text.

The wires 100, 200 are made of a resilient material, highly preferably a metal. The wires 100, 200 must be non-magnetizable, in order to allow the wearer of a filter to undergo an NMR or MRI (Magnetic Resonance Imaging) examination without damage. This film [sic] must also be radiopaques [sic] in order to allow it to be visible during X-ray examination.

The wires 100, 200 may be formed of any appropriate materials known to the person skilled in the art.

By way of non-limiting example, the wires 100, 200 may be made from an alloy chosen from the group comprising the following alloys:
i) copper and nickel and aluminum,
ii) copper and zinc and aluminum,
iii) copper and zinc and aluminum and nickel,
iv) copper and tin and nickel.

A final coating with a thin biocompatible layer, preferably of gold, is made in order to avoid phenomena of corrosion and to ensure biocompatibility.

The diameter $d101$ of the first wire 100 preferably lies between 0.25 and 1 mm. The diameter $d101$ of the first wire 100 is typically of the order of 0.37 mm. The diameter $d201$ of the second wire 200 also preferably lies between 0.25 mm and 1 mm. As previously indicated, the diameter $d201$ of the second wire 200 is preferably less than the diameter $d101$ of the first wire 100, so that the second spiral formed by the wire 200 is more flexible than the first spiral formed by the wire 100. The diameter $d201$ of the second wire 200 is typically of the order of 0.30 mm.

Thus, the filter formed by the two wires 100, 200 can be introduced into a catheter 800 of the "7F" type, that is to say, the magnitude F being equal to 0.33 mm, a catheter of external diameter 2.31 mm and a working internal caliber of the order of 1.77 mm.

The use of a 7F catheter for fitting the filter and withdrawing the latter allows the filter to be fitted and withdrawn through the channel of small veins, for example a vein of the fold of the elbow.

The two wires 100, 200 are preferably made from the same alloy. However, the two wires 100, 200 may be made from a different alloy.

The procedure for producing the filter represented in FIGS. 1 to 3 is essentially as follows. First of all, the two wires 100, 200 are cut to the desired length. The total length of the wires typically lies between 22 and 35 cm. The two wires 100, 200 are wound onto mandrels of appropriate caliber. The winding mandrel of the first wire 100 has a plurality of cross-sections corresponding to the respective diameters $d110$, $d120$, $d130$, of the middle turn 110 and of the lateral turns 120, 130. The winding mandrel of the second wire 200 has a constant cross-section equal to the diameter $d200$ of the turns of the second spiral.

Once wound onto this or these mandrels, the wires 100, 200 are subjected to an appropriate heat treatment known to specialists in the technology of metal wires with a remanent spring effect characteristic.

The operation of connecting the two wires 100, 200, typically by crimping the endpieces 300, 400, can then be carried out.

Finally, as previously indicated, the filter is coated with a biocompatible material, preferably gold, including over the endpieces 300, 400.

The method of fitting and possible withdrawal of the filter represented in FIGS. 1 to 3 will be described below with reference to FIGS. 9 to 15.

Figure 4:
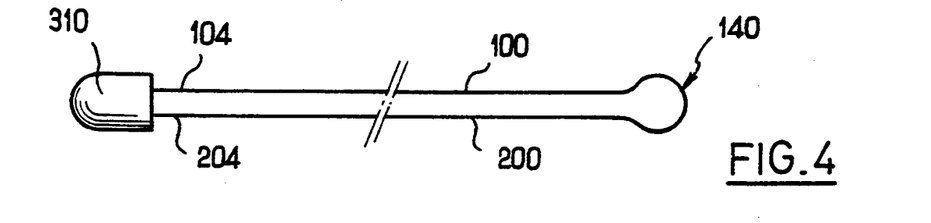
Figure 5:
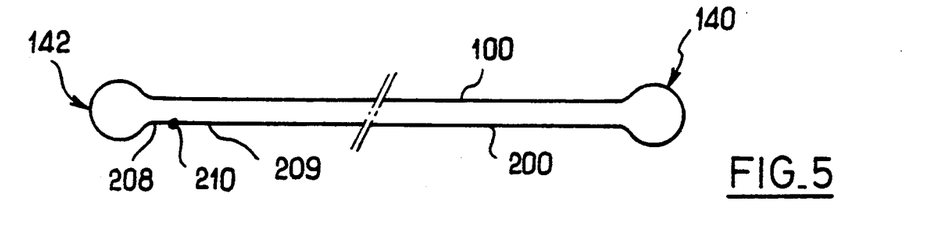
Figure 6:
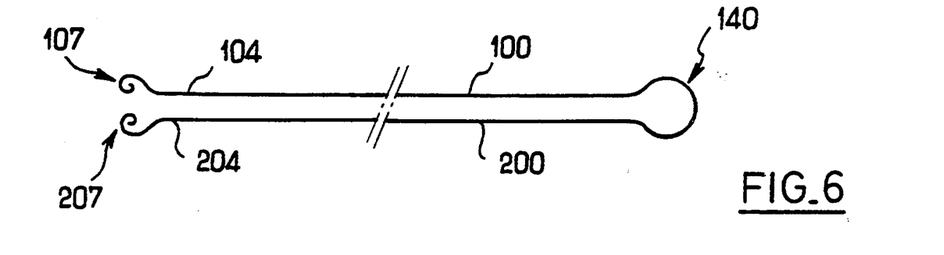

VARIANT EMBODIMENTS REPRESENTED IN FIGS. 4, 5 AND 6

According to the embodiment previously described and represented in FIGS. 1 to 3, the filter is formed by two separated wires 100, 200 connected by their ends.

The wires 100, 200 can be connected together by crimping endpieces 300, 400, or by any other appropriate means such as, for example, by adhesive bonding or soldering.

As a variant, the anti-pulmonary embolism filter according to the present invention can be produced using a single wire, as represented in FIGS. 4 to 6.

According to the embodiment represented in FIG. 4, the single wire is folded on itself substantially half-way along, at 140, in order to form the two spirals 100, 200.

The free ends 104, 204 of the two strands of wire are connected by any appropriate conventional means. This may involve adhesive bonding or soldering. According to FIG. 4, it involves connection using a crimped endpiece 310. The endpiece 310 may correspond to the endpiece 300 or the endpiece 400 which have been described previously. The bend 140 of the wire may form the distal filter end, in which case the ends 104, 204 of the wire form the proximal end of the filter. Conversely, the bend 140 of the wire may form the proximal end of the filter, in which case the ends 104, 204 of the wire form the distal end of the filter.

According to FIG. 5, the single wire is folded two times on itself at 140, 142. The strands 100, 200 of the wire formed between the bends 140, 142 are of substantially the same length. Furthermore, the two ends of the wire 208, 209 are connected together at 210 such that the wire forms a closed loop. The connection 210 may be formed by adhesive bonding, soldering, crimping a bead onto the ends 208, 209, or any other appropriate means.

According to FIG. 6, the single wire is folded on itself substantially half-way along, at 140, in order to form the two spirals 100, 200.

The free ends 104, 204 of the two strands of the wire are separated, but each fitted with an open loop 107, 207, so that the wire does not risk injuring the vena cava receiving the filter.

The single-wire variants can be used for making a filter of the same geometry as that represented in FIGS. 1 to 3, i.e. a filter comprising a first spiral 100 with three turns, namely a middle turn of large diameter and two lateral turns of smaller diameter, and a second spiral 200 of the same sign of helical twisting as the first spiral, comprising a larger number of turns of substantially constant diameter.

Figure 7:
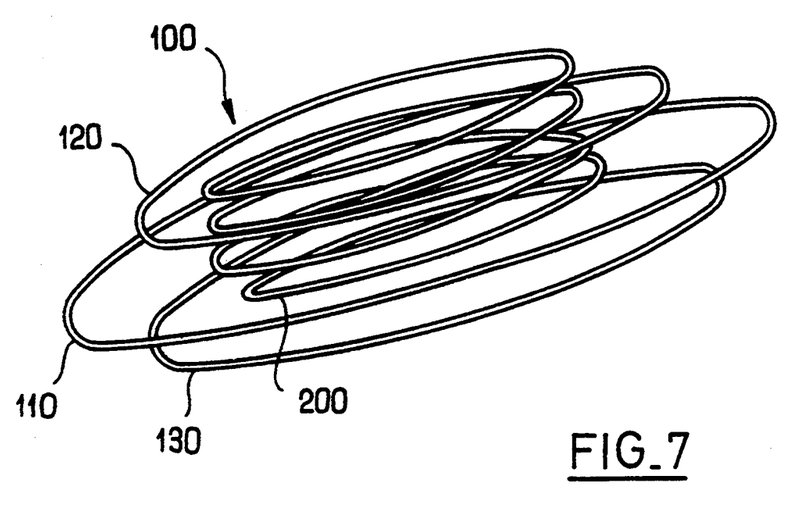
FIG. 7 represents a diagrammatic perspective view of an anti-pulmonary embolism filter in accordance with one variant embodiment of the present invention.

VARIANT EMBODIMENT REPRESENTED IN FIG. 7

The filter represented in FIG. 7 is made using a single wire shaped into a closed loop as illustrated in FIG. 5, which has been described previously.

Moreover, the filter represented in FIG. 7 has the same geometry as that represented in FIGS. 1 to 3. Thus, the filter represented in FIG. 7 comprises two spirals 100, 200.

The first spiral 100 comprises three turns: a middle turn 110 of large diameter and two lateral turns 120, 130 of diameters which are substantially equal to each other but smaller than the middle turn 110.

The second spiral 200 comprises more turns than the first spiral 100, for example four turns, and its turns have substantially constant diameters.

It will be noted that, according to FIGS. 1 to 3, the two spirals 100, 200 are of the same sign of helical twisting. In contrast, according to FIG. 7, the two turns [sic] are of opposite signs of helical twisting. That is to say that the two turns [sic] 100, 200 have opposite handedness according to FIG. 7.

The use of the two spirals 100, 200 of the same signs of helical twisting makes it possible to facilitate the deployment of the filter in the vena cava, at the exit of the fitting catheter, since the two spirals 100, 200 are then deployed in the same general direction.

In contrast, the use of two spirals 100, 200 of opposite signs of helical twisting makes it possible to facilitate movement of the filter through the fitting catheter, since the two spirals then bear on diametrically opposite zones of this catheter and generate substantially symmetrical forces, which prevents blocking of the filter in the catheter.

As a variant, the filter comprising two spirals 100, 200 of opposite signs of helical twisting, represented in FIG. 7, might be made with a single wire of the type illustrated in FIG. 4 or in FIG. 6, or alternatively with two separate wires connected at their ends by adhesive bonding, soldering, crimping of endpieces or any other appropriate means, as previously indicated.

In the case when, as represented in FIG. 6, the free ends 104, 204 of the single filter remain separated, it is possible to make provision for the two spirals 100, 200 to have lengths which are at least slightly different.

According to another derivative variant of FIGS. 1 and 6, it is possible to provide a filter formed using two separate wires connected by only one of their ends, by adhesive bonding, soldering, crimping of an endpiece or any other appropriate means, but left free at their second ends. In this case, it is preferable then to provide loops similar to the loops 107, 207 on these second ends of the wires 100, 200, in order to prevent injury to the vena cava. If the two wires 100, 200 remain separated at one of their ends, they may have lengths which are at least slightly different.

Figure 8:
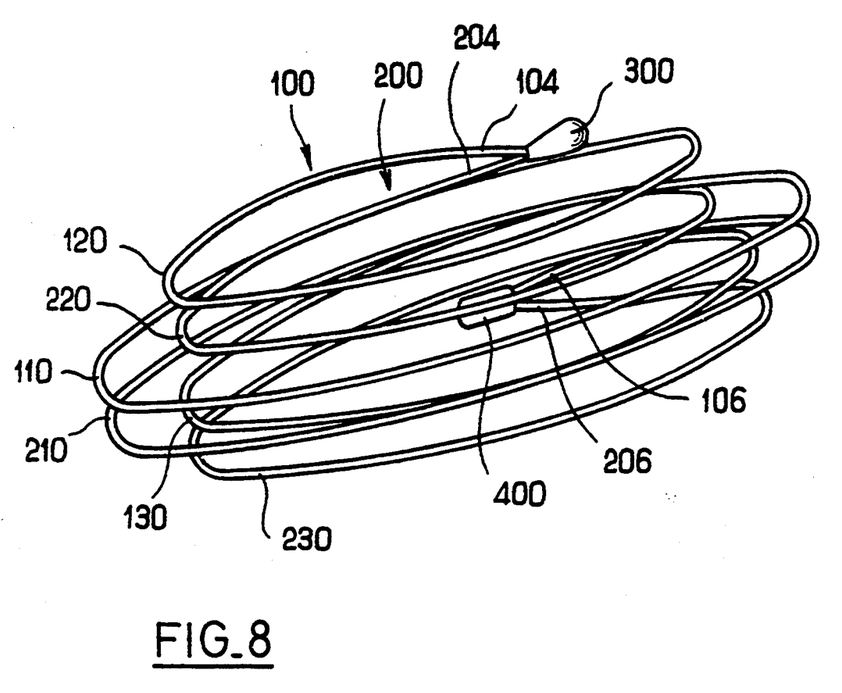
FIG. 8 represents a diagrammatic perspective view of an anti-pulmonary embolism filter in accordance with another variant embodiment of the present invention.

VARIANT EMBODIMENT REPRESENTED IN FIG. 8

The present invention is of course not limited to the particular embodiments of filters which have just been described, but extends to any variants in accordance with its spirit.

Thus for example, as represented in FIG. 8, it is possible to envisage giving the two spirals 100, 200 configurations which are substantially identical to each other and identical to the configuration of the first spiral formed by the wire 100 in FIGS. 1 and 2.

In this case, the two spirals 100, 200 each comprise, as represented in the attached FIG. 8, substantially three turns: a middle turn of larger diameter 110, 210, and two lateral turns, respectively 120, 130 and 220, 230. In order to guarantee a correct filtering effect, the two spirals must be spaced longitudinally. For this purpose, the ends of the two spirals are deformed in respectively opposite longitudinal directions. If required, the pitches of the lateral turns 120, 130, on the one hand, and 220, 230, on the other hand, of the two spirals may be different from one spiral to the other, in order to prevent the strands formed by these lateral turns being attached even if the two middle turns 110, 210 are brought into contact by the resilience of the vena cava. The filter in FIG. 8 may be formed by two separate wires whose two ends are connected by any appropriate conventional means, such as adhesive bonding, soldering or crimping of the endpieces 300, 400. This filter in FIG. 8 may be formed by two separate wires connected together at only one of their ends, by any appropriate conventional means, such as adhesive bonding, soldering or crimping of an endpiece.

The filter of FIG. 8 may also be made with a single wire of the type represented in one of FIGS. 4, 5 or 6.

According to FIG. 8, the two spirals 100, 200 are of the same sign of helical twisting. As a variant, the two spirals 100, 200 might be of opposite signs of helical twisting.

According to yet another variant, the filter may be formed by two spirals of diameters which are constant and identical for the two spirals.

The spirals may be of the same sign of helical twisting or of opposite signs of helical twisting.

These spirals may be formed by two separate wires connected respectively at their two ends, or at only one of their ends.

These spirals may also be formed by a single wire, as illustrated in FIGS. 4, 5 and 6.

Furthermore, the filter in accordance with the present invention may comprise a number of spirals greater than two, for example three spirals, four spirals or more, the diameters of which may or may not be constant. These spirals may or may not all be of the same sign of helical twisting. They may be formed by separate wires connected respectively at their two ends. The wires are then substantially all of the same length. The spirals may be formed by separate wires connected at one of their ends. The spirals may also be formed by a single wire.

It was previously indicated that the first spiral composed of the wire 100 preferably comprises three turns. This arrangement has proven optimal for obtaining a satisfactory filtering effect and correct holding of the filter without risk of migration. A larger number of turns would needlessly increase the length of the wire unwound. This would have the consequence of increasing the difficulty of transfer through the catheter 800. On the other hand, a smaller number of turns would reduce the filtering effect.

However, the definition of the invention need not be strictly limited to a geometry with three turns. It is in fact evident that a filter with a number of turns slightly greater than or less than three would be satisfactory.

FITTING OF THE FILTER

The technique for fitting the filter in accordance with the present invention will now be described with reference to FIGS. 9 to 15, on the basis of a filter with two spirals, of the type represented in FIGS. 1 to 3. This fitting technique is, however, applicable to any one of the variants of the filter in accordance with the invention.

The resilient quality of the wires 100, 200 used, and their small diameter, make it possible, under the effect of slight tension, to make the filter temporarily quasi-straight. In this quasi-straight state, the filter can be introduced into a catheter 800 of small diameter, typically 7F as previously indicated, in order to be transported therein without constraint, both in one direction with a view to implantation in the inferior vena cava and in the other with a view to withdrawal.

The filter can be moved through the aforementioned catheter 800, with a view to fitting in the vena cava, using any appropriate conventional means.

The filter can be moved through the catheter 800 using a pusher of the type described in previous patent applications FR-89 13160 of 9, Oct. 1989 and FR-89 16538 of 14, Dec. 1989. The pusher described in these previous patent applications is diagrammatically illustrated in the attached FIGS. 9 and 10 under the reference 500.

Figure 10:
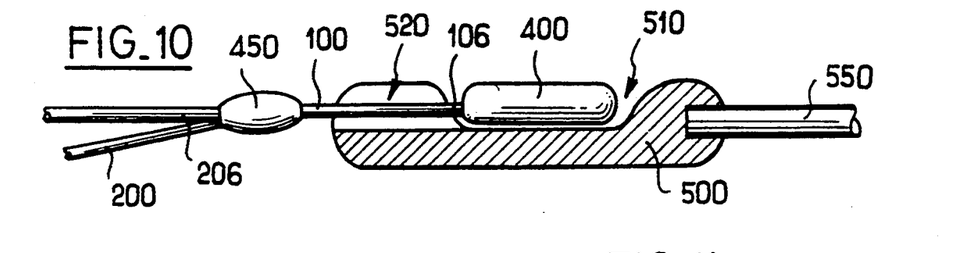
FIG. 10 represents a view similar to FIG. 9, of the same fitting pusher in longitudinal section.

The pusher 500 is fixed to the end of a cable 550, such as a flexible braided steel cable. The cable 550 typically has a diameter of the order of 0.7 mm. Thus, the tension and thrust exerted on the cable 550 make it possible to manipulate the pusher 500 and the filter connected thereto, in the fitting catheter 800. The pusher 500 is formed by a rigid body of rounded outline. The pusher 500 has, substantially half-way along, a lateral recess 510 designed to accommodate one of the endpieces 300, 400 provided at the end of the filter, preferably the end cylinder 400. Furthermore, as represented in FIG. 10, the pusher 500 has, on the other side from the cable 550, a lateral notch 520 which emerges in the recess 510. The notch 520 is designed to accommodate the wire or wires connected to the corresponding endpiece 300 or 400.

Reference may be made to the description given in patent applications FR-89 13160 of 9, Oct. 1989 and FR-89 16538 of 14, Dec. 1989 in order better to understand the operations of fitting the filter using the pusher 500 and the associated cable 550.

It was previously indicated that the two wires 100, 200 may be connected at their ends by crimping the endpiece 300 or 400.

Figure 9:
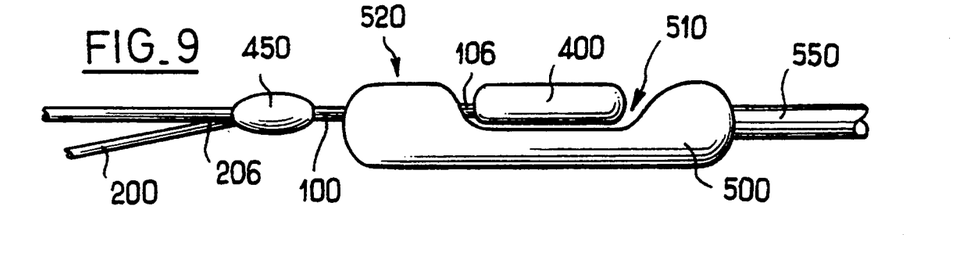
FIG. 9 represents a partial view of one end of the filter in accordance with the present invention, associated with a first fitting pusher.

As diagrammatically represented in FIGS. 9 and 10, as a variant, it is possible to envisage fixing one of the ends, such as the distal end 206, of the second wire 200, set back from the corresponding end 106 of the first wire 100, using an intermediate bead 450 or any other appropriate conventional means such as an adhesive bond or a solder. Because of this, as represented in FIG. 9, only the first wire 100 is engaged in the notch 520 of the pusher. This device makes it possible to use a notch 520 of small width.

The pusher 500 may typically have a length of 10 to 12 mm and a diameter adapted to the internal caliber of the fitting catheter 800, typically of the order of 1.6 mm, in order to be able to slide therein without friction. The endpiece 400 escapes from the associated pusher 500 when the latter emerges from the fitting catheter 800, by virtue of the resilience of the filter, as described in previous patent applications 89 13160 of 9, Oct. 1989 and 89 16538 of 14, Dec. 1989.

Figure 11:
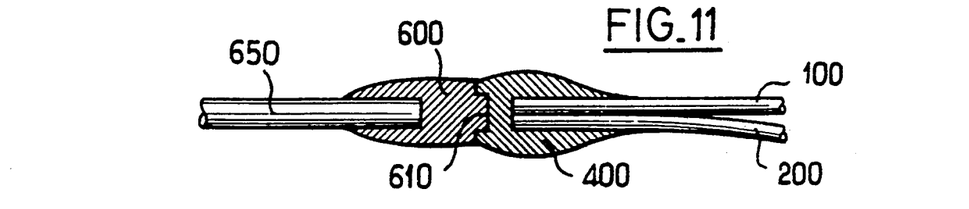
FIG. 11 represents a partial view of one end of the filter in accordance with the present invention, associated with another fitting pusher.
Figure 12:
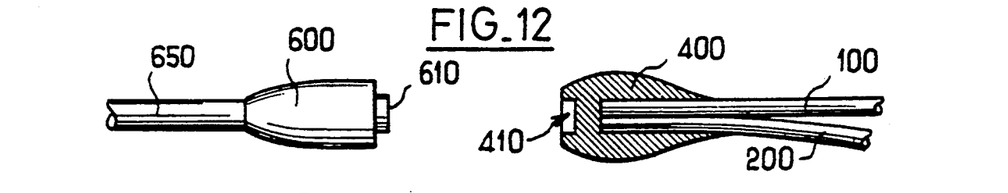
FIG. 12 represents the same end of the filter and the same fitting pusher as in FIG. 11, but in the separated state.

FIGS. 11 and 12 represent another pusher variant capable of transporting the filter through a fitting catheter 800.

Figure 13:
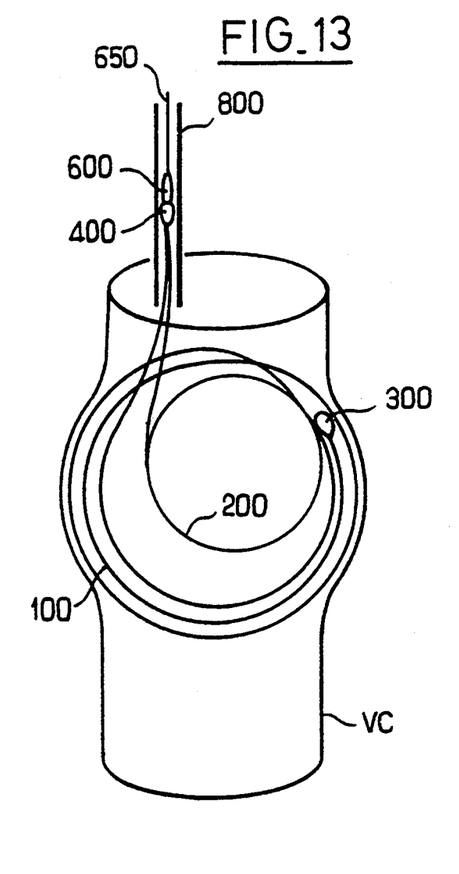
FIGS. 13 and 14 illustrate the steps of fitting the filter in a vena cava.
Figure 14:
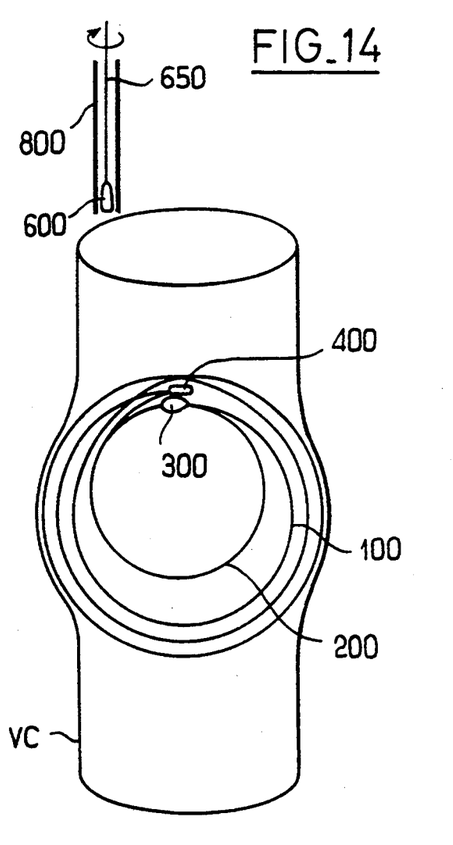

A pusher 600 can be seen in FIGS. 11 and 12 fixed onto a cable 650 similar to the aforementioned cable 550. The pusher 600 is fitted with a structure 610 of the threaded shaft type, capable of being engaged in a corresponding tapped bore 410 made at the end of the endpiece 400 or 300. The external diameter of the pusher 600 must obviously be adapted to allow sliding of the pusher 600 through the fitting catheter 800. The procedure for fitting a filter using the pusher 600 represented in FIGS. 11 and 12 is as follows. The filter composed of the wires 100, 200 is placed in the fitting catheter 800, its endpiece 400 being connected to the pusher 600. The fitting catheter 800 is brought close to the place of implantation of the filter into the inferior vena cava VC, as represented in FIG. 13. The positioning of the catheter 800 is monitored by radiopaque elements provided on the catheter 800, such as for example two thin rings 810, 812 fixed to the end of the latter. (see FIG. 16).

Figure 15:
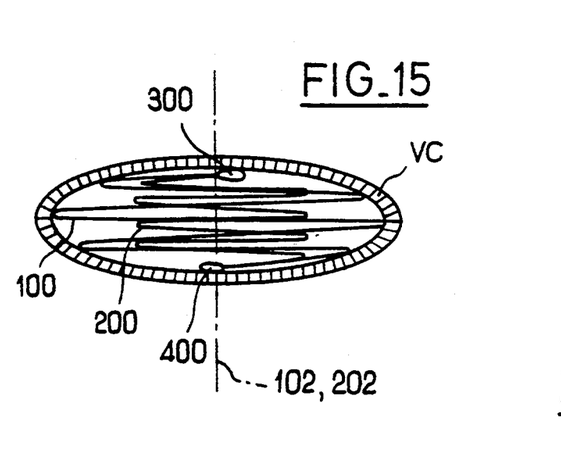
FIG. 15 represents a cross-sectional view of a vena cava equipped with a filter in accordance with the present invention, FIG. 16 diagrammatically represents a presentation and fitting kit in accordance with the present invention.

By pushing on the cable 650, the filter is moved out of the fitting catheter 800 into the inferior vena cava VC (see FIG. 13). At the exit of the catheter 800, the filter returns to its double-spiral configuration represented in FIGS. 1 and 2. The filter is held in place essentially by the middle turn 110 of the first spiral, which bears on the walls of the vena cava VC, in order to prevent any risk of migration of the filter in the vena cava VC. The axes 102, 202 of the spirals are then orthogonal to the longitudinal axis of the vena cava VC. Since the diameter of the middle turn 110 is of the order of magnitude of half the circumference of the inferior vena cava, the latter is greatly flattened after implantation of the filter, as represented in FIG. 15. The filter thereby leads to a great decrease in the passage cross-section of the blood flow through the vena cava VC. The filtering of clots coming from the blood circulation is due to two cumulative effects: the flattening of the vena cava in the implantation zone, as previously indicated, on the one hand, and the presence of various arcs composed of the two spirals 100, 200 across the vena cava, on the other hand, as represented in FIG. 15.

On this point, the second spiral 200 which has a larger number of turns than the first spiral because of its smaller mean diameter plays a dominant role.

In order to separate the filter from the pusher 600 and from the associated cable 650, once the filter is correctly fitted, it is sufficient to rotate the cable 650 in order to unscrew the structure 610 from the complementary tapped bore 410, as illustrated in FIG. 12.

Clearly, if the doctor observes incorrect fitting of the filter, he may withdraw the latter into the fitting catheter 800, as long as the pusher 600 remains connected to the endpiece 400.

As a variant, it is possible to envisage making the threaded shaft 610 on the endpiece 400 and the tapped bore 410 in the pusher 600. In this case, this shaft 610 must be shaped so that it is not traumatizing for the vena cava.

PRESENTATION OF THE FILTER

Figure 16:
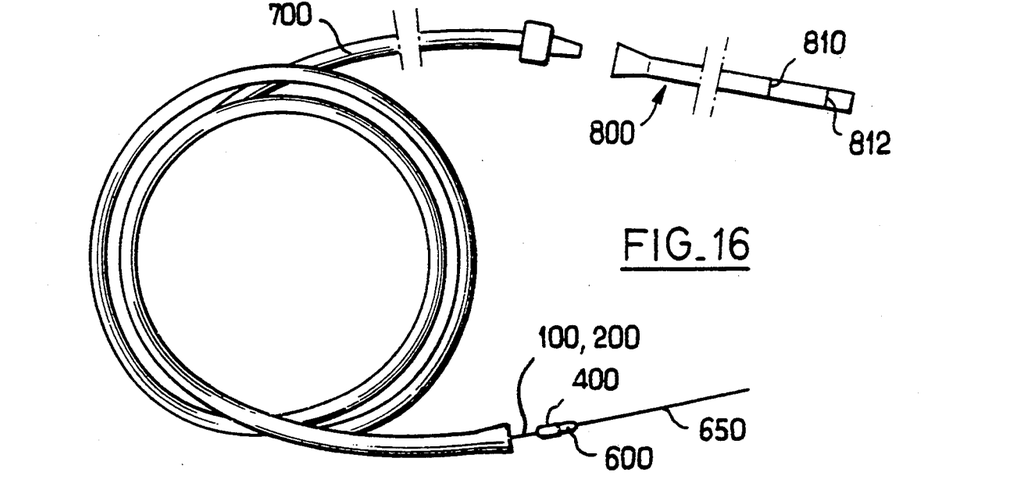

During storage, the filter may be placed in an appropriate container tube 700, as represented in FIG. 16. The filter in accordance with the present invention may then be sold in the form of a kit comprising the filter composed of two wires 100, 200 and placed in the aforementioned container tube 700, a fitting catheter 800 designed to be connected to the container tube 700, and a pusher 500 or 600 connected to the end of a cable 550 or 650.

However, the container tube 700 is not essential.

The anti-pulmonary embolism filter in accordance with the present invention may be packaged in a blister-pack. It is then introduced into the fitting catheter 800, by the doctor, just before implantation.

MEANS FOR WITHDRAWING THE FILTER

The configuration of the filter, which is non-traumatizing for the vein, prevents any penetration of the vein wall by parts of this filter. Physiologically, after implantation, the arcs of the turns in contact with the vein wall are progressively covered with endothelial tissue. The time for permanent fixing of the filter in the vein is at least of the order of a fortnight, so that, during this period, it is still possible to withdraw it percutaneously, that is to say without a surgical operation.

This withdrawal may be carried out as previously describing using the means disclosed in patent applications FR-89 13160 of 9, Oct. 1989 and FR-89 16538 of 14, Dec. 1989.

Figure 17:
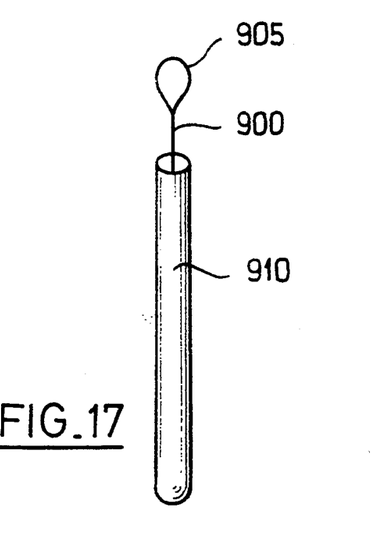
FIG. 17 represents a diagrammatic view of a withdrawal device of the lasso type.

Withdrawal of the filter can also be carried out using the "lasso"-type device diagrammatically represented in FIG. 17.

Means of the "lasso" type are diagrammatically illustrated in FIG. 17. They essentially comprise a wire 900 fitted with a loop 905 and engaged in a catheter 910.

In order to withdraw the filter from an inferior vena cava, it is sufficient to bring the catheter 910 to the place of implantation, to grasp one of the endpieces 300, 400 and thus to withdraw the filter into the withdrawal catheter 910.

Figure 27:
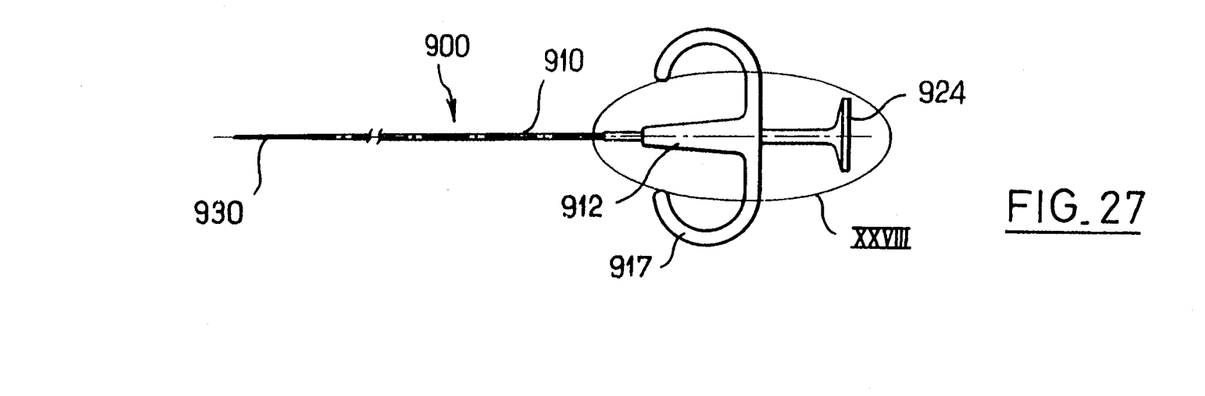
FIG. 27 represents a second embodiment of an intra-catheter clamping means in accordance with the present invention.
Figure 28:
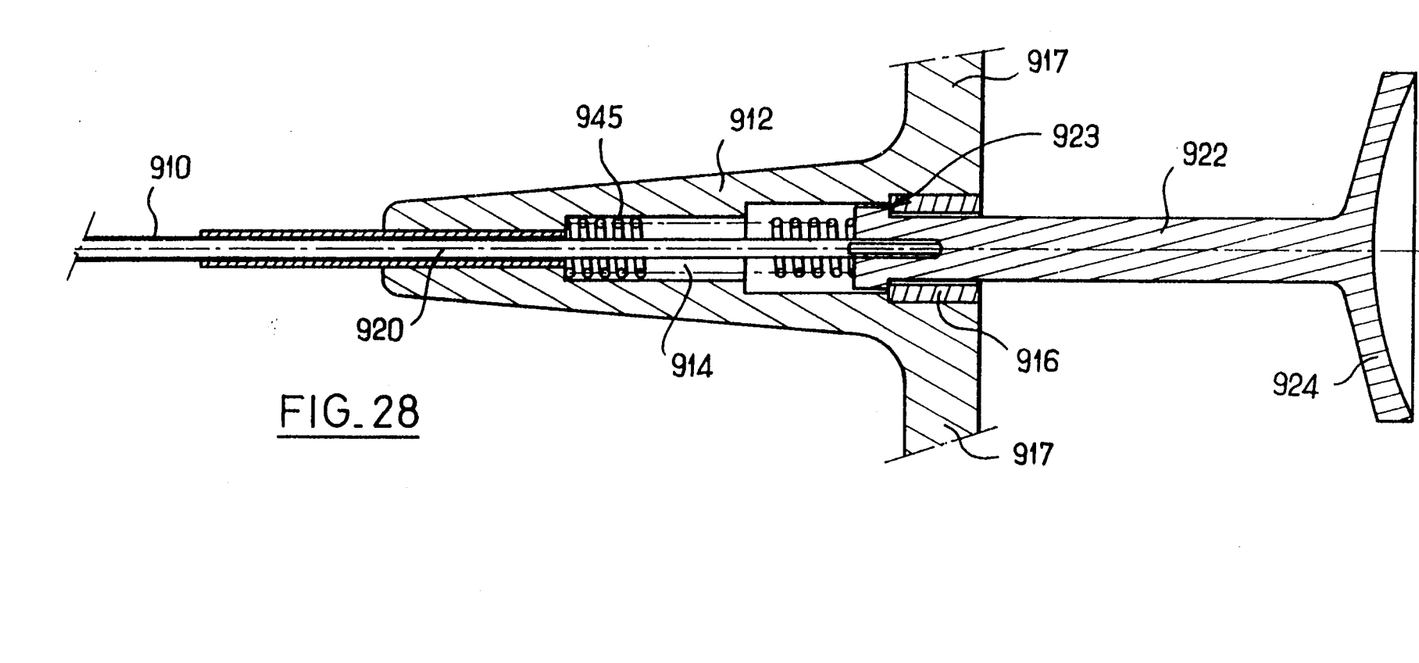
FIG. 28 represents a detailed view, on an enlarged scale, of this second embodiment of the intra-catheter clamping means according to the present invention.

The filter can also be acted on using an instrument of the type represented in FIGS. 18 to 26, or of the type represented in FIGS. 27 and 28.

The instrument represented in FIGS. 18 to 26 will now be described.

Figures 18, 19, 20, 21, 22, 23, 24, 25, 26:
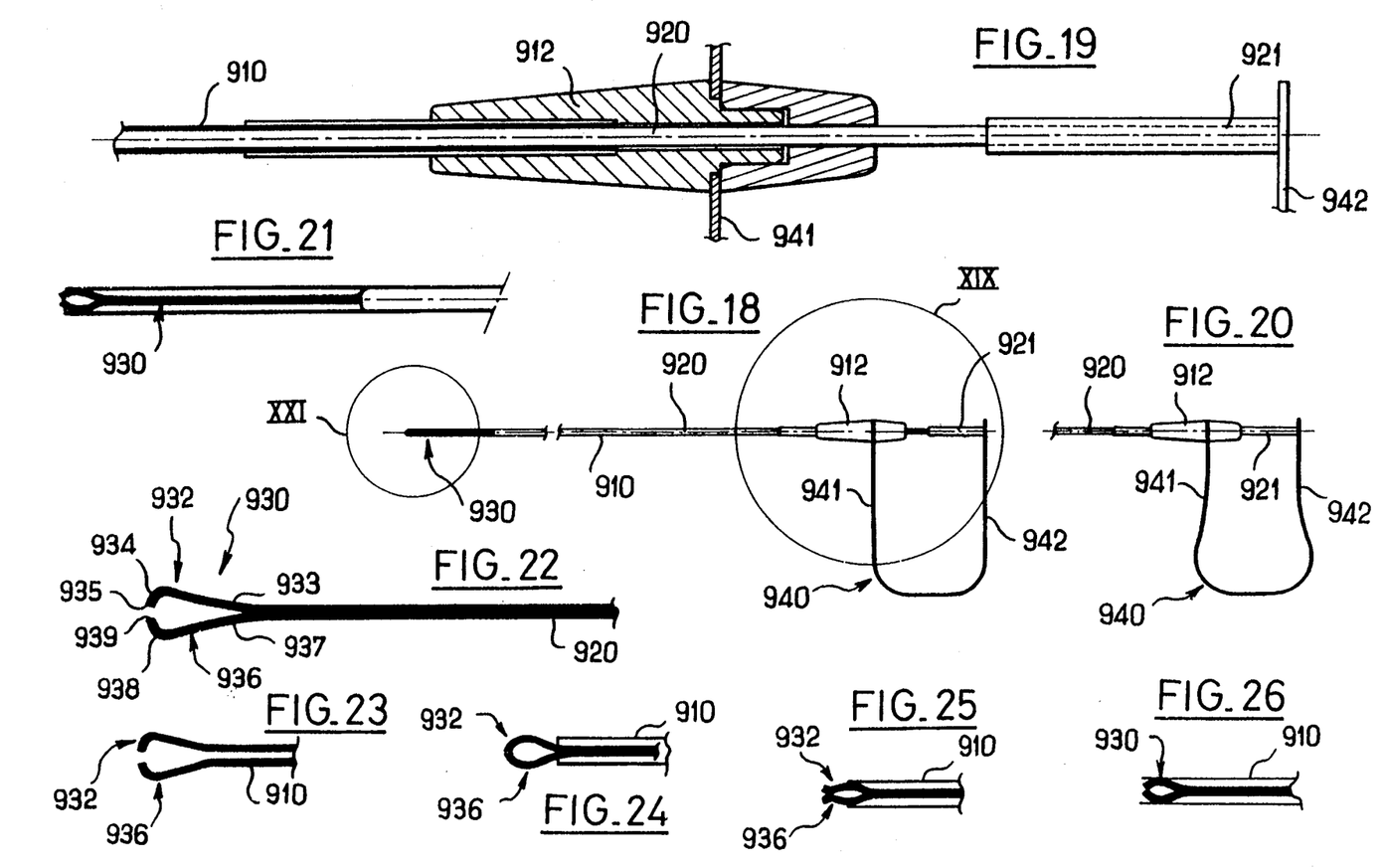
FIG. 18 represents a first embodiment of an intra-catheter clamping means in accordance with the present invention, designed for withdrawing the anti-pulmonary embolism filter.
FIG. 19 represents a detailed view, on an enlarged scale, of the same clamping means.
FIG. 20 represents a partial view of the same clamping means, in the actuated state.
FIG. 21 represents another detailed view, on an enlarged scale, of the same clamping means.
FIGS. 22, 23, 24, 25 and 26 represent various steps in the operation of this clamping means.

This instrument 900 essentially comprises a tube 910 which accommodates an elongate pusher 920 fitted with a clamping means 930.

The tube 910 and the pusher 920 should be made of fairly flexible material, so as to bend in order to be introduced into a catheter which is itself placed in a vessel leading to the point of implantation of the filter.

The pusher 920 can slide through the tube 910. The clamping means 930 is integral with the proximal end of the pusher 920. The clamping means 930 comprises two resilient jaws 932, 936.

The two resilient jaws 932, 936 are preferably identical, and therefore symmetrical with respect to the axis of the pusher 920.

The two jaws 932, 936 are configured so as to adopt at rest, in the absence of an external constraint, the configuration illustrated in FIG. 22.

That is to say, starting from their zone of connection onto the pusher 920, the jaws 932, 936 diverge at 933, 937 towards their proximal ends, then converge at 934, 938.

Thus, the two ends 932, 936 have concavities which face each other.

At rest, the free ends 935, 939 of the two jaws are spaced apart in order to allow a wire of the filter to be placed between them.

However, the pusher 920 and the clamping means 930 are pressed into a position of withdrawal inside the tube 910 by return means 940.

The return means 940 are provided at the distal end of the tube 910 and of the pusher 920.

These return means 940 may form the subject of numerous embodiments.

In the case in point, according to the embodiment represented in FIG. 18, these return means 940 comprise a resilient U-shaped plate, for example a metal plate. More precisely, this plate 940 is fixed, respectively by these [sic] two parallel arms 941, 942, onto an endpiece 912 integral with the distal end of the tube 910 and the distal end 921 of the pusher 920.

Thus, as represented in FIGS. 18, 21 and 26, at rest, the jaws 932, 936 of the clamping means 930 are pressed, in a retracted and clamped position, into the tube 910.

In order to open the clamping means 930, it is sufficient to press together the two arms 941, 942 of the plate 940, as represented in FIG. 20. Thus, the pusher 920 is moved in translation through the tube 910 and the clamping means 930 then emerges at the proximal end thereof. The jaws 932, 936 thus return to their rest position illustrated in FIGS. 22 and 23. The two jaws 932, 936 are separated. In this position, a wire of the filter can be engaged between the jaws 932, 936. In order to grasp this wire, it is sufficient to release the plate 940, whilst taking care to hold the wire between the jaws 932, 936. More precisely, it is necessary for this purpose, whilst holding the position of the pusher 920, to allow the tube to move in the proximal direction under the effect of the pressing of the plate 940.

As represented in FIG. 24, the tube 910 then bears on the external diverging surfaces of the jaws 932, 936, in order to press them closed.

Depending on the flexibility of the wire of the filter, the withdrawal of the jaws 932, 936 into the tube 910 may be of greater or lesser degree.

The clamping means represented in FIGS. 18 to 26 can be used either for fitting the filter or for withdrawing it through a catheter.

It is easy to see that the structure of the pusher 920 and of the clamping means 930 makes it possible to use a tube 910, and therefore an associated catheter, of small diameter.

The variant embodiment of the instrument represented in FIGS. 27 and 28 will now be described.

An instrument 900 is seen in these figures which essentially comprises a tube 910 which accommodates an elongate pusher 920 fitted with a clamping means 930.

The instrument in FIGS. 27 and 28 differs from that represented in FIGS. 18 to 20 essentially in that the U-shaped plate is replaced by a spiral spring 945. This spring 945 is placed in a housing 914 formed in the endpiece 912 connected to the distal end of the tube 910. The spring 945 is placed on the distal end of the pusher 920, between the bottom of the housing 914 and an endpiece 922 integral with the distal end of the pusher 920.

Preferably, means are provided limiting the movement of the pusher 920 in the distal direction under the effect of the spring 945. These limitation means may form the subject of numerous embodiments. According to FIG. 28, these limitation means comprise a shoulder 923 which are [sic] formed on the endpiece 922 and bear on a ring 916 connected to the endpiece 912.

The proximal end of the pusher 920 is fitted with a clamping means 930 in accordance with that previously described with reference to FIGS. 21 to 26.

Furthermore, the presence of gripping means 917, 924, respectively on the endpieces 912 and 922 connected to the distal ends of the tube 910 and of the pusher 920, will be observed on examining FIGS. 27 and 28.

These gripping means are intended to facilitate actuation of the instrument. They may form the subject of numerous variants. For this reason, these gripping means will not be described in further detail below.

Figure 29:
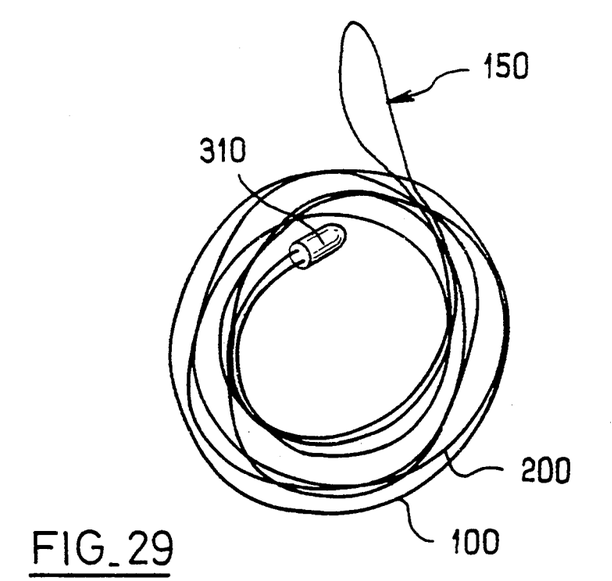
FIG. 29 represents a plan view of a filter in accordance with another variant embodiment of the present invention.
Figure 30:
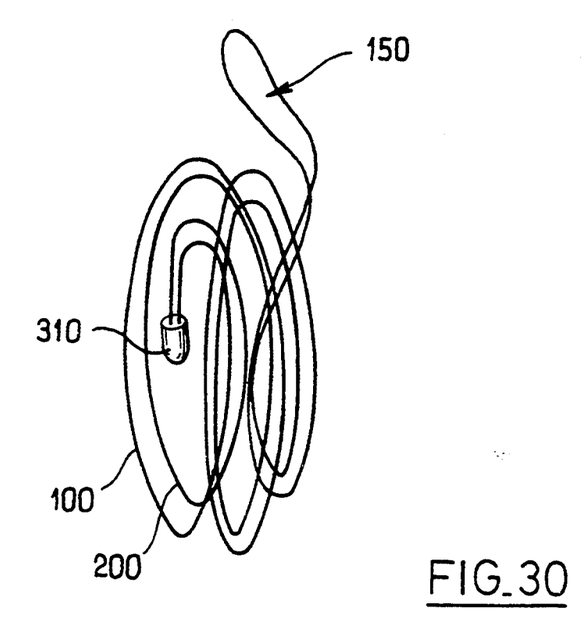
FIG. 30 represents a profile view of the filter illustrated in FIG. 29, FIGS. 31, 32 represent the main steps in fitting this filter in a vena cava.

VARIANT EMBODIMENT REPRESENTED IN FIGS. 29 AND 30

FIGS. 29 and 30 represent a variant embodiment of the filter in accordance with the present invention, adapted to facilitate withdrawal.

The filter represented in FIGS. 29 and 30 is essentially characterized with respect to the filters previously described, in that one of the ends of the two spirals 100, 200 constitutes a closed loop 150 projecting radially on the outside of the spirals.

According to the representation given in FIGS. 29 and 30, the loop 150 is formed at the bend made on a single wire, namely the bend referenced 140 or 142 in FIGS. 4, 5 or 6.

The loop 150 might however be formed at the ends of the wires 100, 200 fitted with endpieces 300, 310 or 400.

The length of the loop 150 may typically be of the order of 1.5 cm, the total length of the wire portion constituting this loop being of the order of 3 cm.

The loop 150 has a general ovoid shape.

Figure 31:
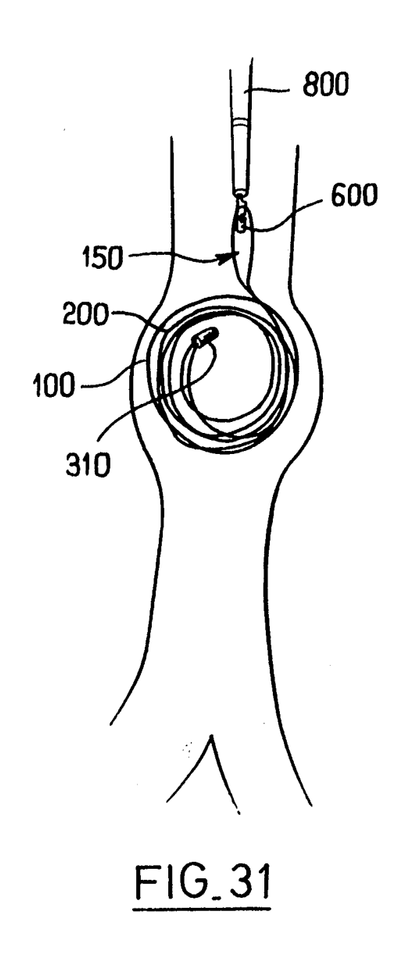

FIG. 31 shows the fitting of the filter, with the loop 150 above the double spiral, using a pusher 600 and a catheter 800 as previously described.

It will be noted that the filter is grasped at the loop 150 by the pusher 600.

Figure 32:
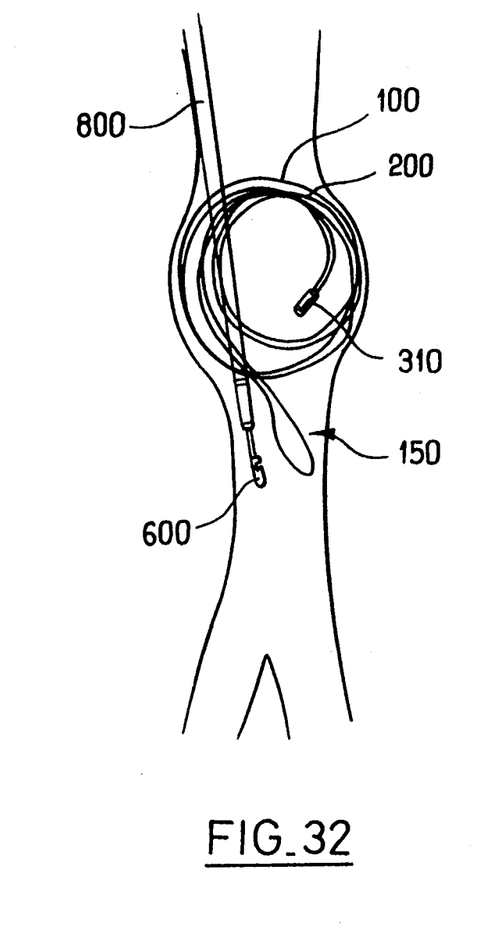

FIG. 32 shows the fitting of the filter, with the loop 150 below the double spiral, using an identical pusher 600 and a catheter 800.

Figure 33:
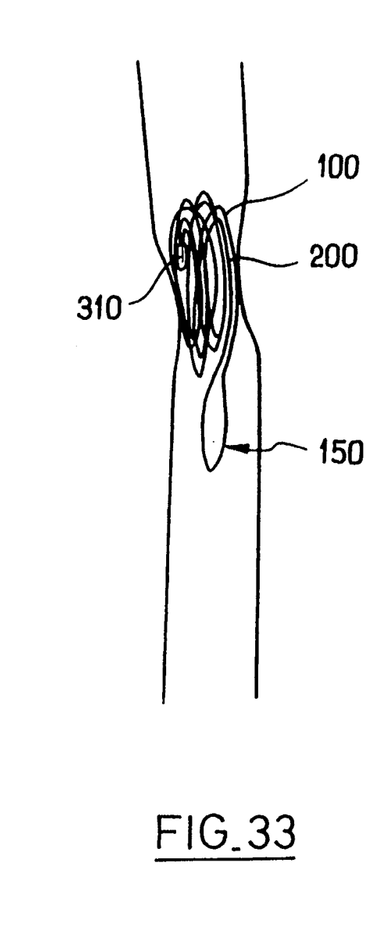
FIG. 33 represents a profile view of the vena cava after fitting the filter, and FIGS. 34, 35 and 36 diagrammatically represent the steps of withdrawing the filter illustrated in FIGS. 29 and 30.

FIG. 33 illustrates, seen in profile, the vena cava flattened by the filter in accordance with the invention.

Figure 34:
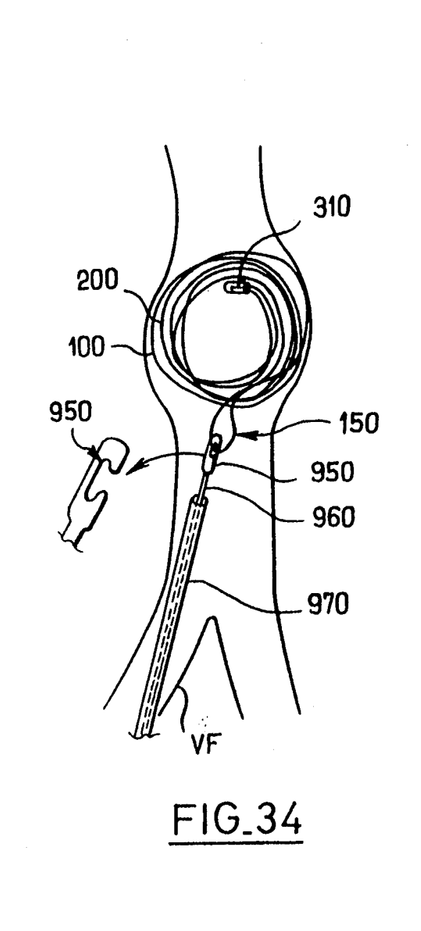
Figure 35:
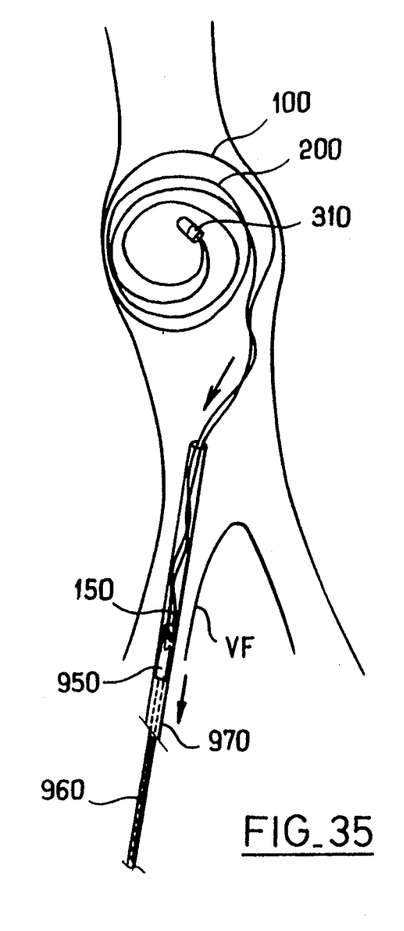
Figure 36:
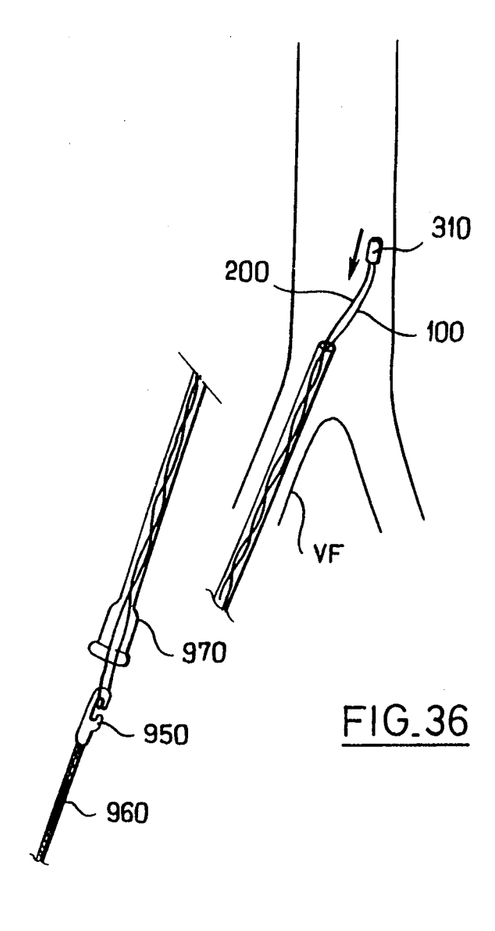

FIGS. 34 to 36 illustrate the withdrawal of this filter using a tool formed by a hook 950 integral with the end of a cable 960 placed in a catheter 970.

As represented in FIG. 34, the loop 150 of the filter can be grasped by the hook 950, and the filter can thus be pulled fully into the catheter 970, as represented in FIGS. 35 and 36, before being withdrawn from the place of implantation, with this catheter, for example through the vena femoralis VF.

The combination of the loop 150 and the hooked withdrawal tool 950 forms a simple and efficient means for withdrawing the filter through a femoral path. This device avoids in particular any curvature and/or any tangling of the filter.

This loop 150 also contributes to the filtering effect, since it intersects the blood flow two times.

The loop 150 is shaped onto the double spiral using the heat treatment mentioned hereinabove which is used for generating the double spiral.

It is understood that the present invention is not limited to the particular embodiments which have just been described, but extends to any variants in accordance with its spirit.

For example, although according to the embodiments previously described and represented in the attached figures the various turns are substantially circular, the use of turns with different configurations can be envisaged, for example generally oval oblong turns or other turns.

We claim:

1. Anti-pulmonary embolism filter made of resilient wire having a remanent spring effect shaped into a spiral structure comprising at least one first non-planar spiral continuous with and superimposed on at least one second non-planar spiral, the first spiral having two lateral turns connected by at least one middle turn having a diameter greater than each of the lateral turns, and the second spiral having turns having diameters no greater than the middle turn of the first spiral, the first and second spirals each having two ends and being joined together at least at one of their respective ends.

2. Anti-pulmonary embolism filter according to claim 1, characterized in that the first and second spirals each comprise a distinct wire having two ends, the distinct wires being joined together at least at one end of each wire.

3. Anti-pulmonary embolism filter according to claim 2, characterized in that the distinct wires are joined together at each of their respective ends.

4. Anti-pulmonary embolism filter according to claim 2, characterized in that the distinct wires are joined together at only one of their respective ends.

5. Anti-pulmonary embolism filter according to claim 2, characterized in that the wires are connected by means selected from the group consisting of adhesive bonding, soldering, and crimping.

6. Anti-pulmonary embolism filter according to claim 1, characterized in that the first and second spirals are formed by a single wire having two ends folded on itself.

7. Anti-pulmonary embolism filter according to claim 6, characterized in that the two ends of the single wire are joined together by means selected from the group consisting of adhesive bonding, soldering, and crimping.

8. Anti-pulmonary embolism filter according to claim 6, characterized in that the two ends of the single wire are fitted with open loops.

9. Anti-pulmonary embolism filter according to claim 6, characterized in that the single wire is folded on itself substantially half-way along.

10. Anti-pulmonary embolism filter according to claim 1, characterized in that the filter has at least one end which is formed by a bend in the resilient wire.

11. Anti-pulmonary embolism filter according to claim 1, characterized in that the filter has at least one end having a discontinuity in curvature in order to facilitate withdrawal of the filter by grasping the end.

12. Anti-pulmonary embolism filter according to claim 1, characterized in that the first and the second spirals are of opposite signs of helical twisting.

13. Anti-pulmonary embolism filter according to claim 1, characterized in that the first and the second spirals are of the same signs of helical twisting.

14. Anti-pulmonary embolism filter according to claim 1, characterized in that the spirals have substantially the same length.

15. Anti-pulmonary embolism filter according to claim 1, characterized in that the resilient wire is made of metal.

16. Anti-pulmonary embolism filter according to claim 1, characterized in that the resilient wire is made of an alloy selected from the group consisting of (i) copper and nickel and aluminum, (ii) copper and zinc and aluminum, (iii) copper and zinc and aluminum and nickel, and (iv) copper and tin and nickel.

17. Anti-pulmonary embolism filter according to claim 1, characterized in that the whole of the filter is coated with a thin layer of gold.

18. Anti-pulmonary embolism filter according to claim 1, characterized in that the turns of the second spiral have diameters substantially identical to each other and less than the diameter of the middle turn of the first spiral.

19. Anti-pulmonary embolism filter according to claim 1, characterized in that the second spiral has four turns.

20. Anti-pulmonary embolism filter according to claim 1, characterized in that the second spiral has a configuration identical to the first spiral that comprises three non-touching turns of a middle turn and two lateral turns of smaller diameter than the middle turn, the first and second spirals being mutually offset.

21. Anti-pulmonary embolism filter according to claim 20, characterized in that the diameter of the middle turn in each spiral is greater than 16 mm.

22. Anti-pulmonary embolism filter according to claim 20, characterized in that the diameter of the middle turn in each spiral is substantially equal to half the circumference of the vena cava in the zone where the filter is to be implanted.

23. Anti-pulmonary embolism filter according to claim 22, characterized in that the diameters of the two lateral turns in each spiral are substantially equal.

24. Anti-pulmonary embolism filter according to claim 1, characterized in that the turns of the first spiral are coaxial and the turns of the second spiral are coaxial but off-centered with respect to the turns of the first spiral.

25. Anti-pulmonary embolism filter according to claim 1, characterized in that the diameter of each turn of the second spiral lies between one half and one third of the diameter of the middle turn of the first spiral.

26. Anti-pulmonary embolism filter according to claim 1, characterized in that the first and second spirals comprise a plurality of turns of constant and identical diameters, the two spirals being offset from each other.

27. Anti-pulmonary embolism filter according to claim 1, characterized in that the first and the second spirals are formed, respectively, of wires of different diameters.

28. Anti-pulmonary embolism filter according to claim 1, characterized in that the wire of the first spiral has a diameter greater than the wire of the second spiral.

29. Anti-pulmonary embolism filter according to claim 1, characterized in that the resilient wire in each spiral has a diameter between 0.25 mm and 1 mm.

30. Anti-pulmonary embolism filter according to claim 1, characterized in that the resilient wire of the first spiral has a diameter of about 0.37 mm.

31. Anti-pulmonary embolism filter according to claim 30, characterized in that the wire of the second spiral has a diameter of about 0.30 mm.

32. Anti-pulmonary embolism filter according to claim 1, characterized in that the resilient wire forming each spiral has a length between 22 and 35 cm.

33. Anti-pulmonary embolism filter according to claim 1, characterized in that the diameter of the middle turn is at least 1.25 times the diameter of each of the lateral turns.

34. Anti-pulmonary embolism filter according to claim 1, characterized in that the diameter of the middle turn is at least 1.4 times the diameter of each of the lateral turns.

35. Anti-pulmonary embolism filter according to claim 1, characterized in that the turns of each spiral have substantially equal pitches.

36. Anti-pulmonary embolism filter according to claim 1, characterized in that the first spiral has a pitch of at least 3 mm.

37. Anti-pulmonary embolism filter according to claim 1, characterized in that the filter has an axial thickness of at least 9 mm.

38. Anti-pulmonary embolism filter according to claim 1, characterized in that the filter has an axial thickness and the diameter of the middle turn is at least twice the axial thickness.

39. Anti-pulmonary embolism filter according to claim 1, characterized in that each spiral comprises a distinct wire having two ends fitted with rounded radiopaque endpieces.

40. Anti-pulmonary embolism filter according to claim 39, characterized in that at least one of the endpieces is fitted with a threaded or tapped structure which can interact with a complementary pusher for fitting the filter.

41. Anti-pulmonary embolism filter according to claim 1, characterized in that it comprises more than two spirals.

42. Anti-pulmonary embolism filter according to claim 1, characterized in that one of the first and second spirals has an end constituting a closed loop projecting radially outside of the spirals.

43. Anti-pulmonary embolism filter according to claim 42, characterized in that the closed loop has a length of about 1.5 cm.

44. Presentation and fitting kit, characterized in that it comprises:
- a filter in accordance with claim 1,
- a catheter which can receive the filter in a sliding manner, and
- means capable of transporting the filter in the catheter.

45. Kit according to claim 44, characterized in that the means capable of transporting the filter comprises a pusher fitted with a threaded or tapped structure capable of interacting with a complementary endpiece of the filter.

46. Kit according to claim 44, characterized in that it further comprises a withdrawal instrument comprising a flexible tube which accommodates a flexible pusher fitted with a clamping means at its proximal end.

47. Kit according to claim 46, characterized in that the clamping means is formed by two symmetrical resilient jaws pressed apart at rest.

48. Kit according to claim 46, characterized in that it further comprises resilient means pressing the pusher and the clamping means in a retracted rest position in the flexible tube.

49. Anti-pulmonary embolism filter according to claim 1, wherein the first and the second spirals are connected respectively at their two ends and have substantially the same length.

50. Anti-embolism filter for implanting in a vena cava so as to retain any clot migrating with the blood before said clot penetrates into the heart, to avoid pulmonary embolism while allowing free flowing of the blood in the vena cava, said filter being made of resilient wire having a remanent spring effect shaped into a spiral structure comprising at least one first non-planar spiral continuous with and superimposed on at least one second non-planar spiral, the first spiral having two lateral turns connected by at least one middle turn having a diameter greater than 16 mm and greater than each of the lateral turns, in order to ensure that the filter is optimally held in place by flattening of the vena cava when said filter is implanted in said vena cava with its axis perpendicular to the axis of said vena cava, and the second spiral having turns having diameters no greater than the middle turn of the first spiral, the first and the second spirals each having two ends and being joined at least at one of their respective ends.

51. Anti-embolism filter according to claim 50, wherein the first and the second spirals are connected respectively at their two ends and have substantially the same length.

52. Anti-embolism filter according to claim 50, wherein the first and the second spirals are made from a single wire folded on itself substantially half-way along.

53. Anti-embolism filter according to claim 50, wherein one of the ends of the two spirals constitutes a closed loop projecting radially outside of the spirals for facilitating withdrawal of the filter by grasping this loop.

54. Anti-embolism filter according to claim 50, wherein the second spiral comprises two lateral turns connected by at least one middle turn having a diameter greater than each of the lateral turns.

55. Anti-pulmonary embolism filter made of a resilient wire having a remanent spring effect folded on itself substantially half-way along and comprising at least one first non-planar spiral continuous with and superimposed on at least one second non-planar spiral, the first spiral having two lateral turns connected by at least one middle turn having a diameter greater than each of the lateral turns, and the second spiral having turns having diameters no greater than the middle turn of the first spiral.

56. Anti-pulmonary embolism filter according to claim 55, wherein the first and second spirals each have two ends, are joined together at each of their respective ends, and have substantially identical lengths.

57. Anti-pulmonary embolism filter according to claim 55, wherein the first and second spirals each have two ends and one of the ends of the first and second spirals constitutes a closed loop projecting radially outside of the spirals for facilitating withdrawal of the filter by grasping this loop.

58. Anti-pulmonary embolism filter according to claim 55, wherein the second spiral comprises two lateral turns connected by at least one middle turn having a diameter greater than each of the lateral turns.

59. Anti-pulmonary embolism filter made of resilient wire having a remanent spring effect shaped into a spiral structure comprising at least one first non-planar spiral continuous with at least one second non-planar spiral, the first and the second spirals having substantially the same length, each spiral having two ends and being joined together at each of their respective ends, the first spiral having two lateral turns connected by at least one middle turn having a diameter greater than each of the lateral turns, and the second spiral having turns having diameters no greater than the middle turn of the first spiral.

60. Anti-embolism filter according to claim 59, wherein the first and the second spirals are made from a single wire folded on itself substantially half-way along.

61. Anti-embolism filter according to claim 55, wherein one of the ends of the first and second spirals constitutes a closed loop projecting radially outside of the spirals for facilitating withdrawal of the filter by grasping this loop.

62. Anti-embolism filter according to claim 55, wherein the second spiral comprises two lateral turns connected by at least one middle turn having a diameter greater than each of the lateral turns.

63. Anti-pulmonary embolism filter according to claim 1, characterized in that the filter has an axial thickness and the diameter of the middle turn is at least 2.5 times the axial thickness.

* * * * *